US009308118B1

(12) United States Patent  
Dupree et al.

(10) Patent No.: US 9,308,118 B1
(45) Date of Patent: Apr. 12, 2016

(54) URINE COLLECTION DEVICE (71) Applicant: Charles B. Dupree, Riviera Beach, FL (US)

(72) Inventors: Charles B. Dupree, Singer Island, FL (US); Donna Lou McCormack, North Palm Beach, FL (US); Robert G. Baker, Boynton Beach, FL (US)

(73) Assignee: Charles B. Dupree, Riviera Beach, FL (US)

( * ) Notice: Subject to any disclaimer, the term of this patent is extended or adjusted under 35 U.S.C. 154(b) by 0 days.

(21) Appl. No.: 14/524,593

(22) Filed: Oct. 27, 2014

(51) Int. Cl.
A61F 5/44 (2006.01)
A61F 2/00 (2006.01)
A61F 5/453 (2006.01)
A61F 5/441 (2006.01)

(52) U.S. Cl.
CPC .............. A61F 5/4408 (2013.01); A61F 5/441 (2013.01); A61F 5/453 (2013.01)

(58) Field of Classification Search
CPC ...................................... A61F 2/00; A61F 5/44
USPC .......................................... 604/349, 351, 353
See application file for complete search history.

(56) References Cited

U.S. PATENT DOCUMENTS

| | | | |
|---|---|---|---|
| 4,568,340 A | 2/1986 | Giacalone | |
| 4,731,070 A | 3/1988 | Koci | |
| 4,769,020 A | 9/1988 | Eaton | |
| 4,790,834 A * | 12/1988 | Austin | A61F 5/453 600/580 |
| 5,009,649 A * | 4/1991 | Goulter | A61F 5/453 604/349 |
| 5,275,592 A | 1/1994 | Grizzaffi | |
| 5,618,277 A | 4/1997 | Goulter et al. | |
| 5,618,279 A | 4/1997 | Pudlo | |
| 5,662,630 A | 9/1997 | Raynie | |
| 5,695,485 A | 12/1997 | Duperret et al. | |
| 5,797,890 A | 8/1998 | Goulter et al. | |
| 5,827,247 A | 10/1998 | Kay | |
| 5,830,932 A | 11/1998 | Kay | |
| 6,209,543 B1 | 4/2001 | Star | |
| 6,248,096 B1 * | 6/2001 | Dwork et al. | 604/349 |
| 6,569,135 B1 | 5/2003 | Mula | |
| 8,187,238 B1 | 5/2012 | Dupree | |
| 2007/0043329 A1 | 2/2007 | Evans | |
| 2007/0073252 A1 | 3/2007 | Forgrave | |
| 2008/0243097 A1 | 10/2008 | Goss | |
| 2009/0270822 A1 | 10/2009 | Medeiros | |

* cited by examiner

Primary Examiner — Tatyana Zalukaeva
Assistant Examiner — Sara Sass
(74) Attorney, Agent, or Firm — Fleit Gibbons Gutman Bongini & Bianco PL; Thomas Grzesik; Jon Gibbons (57) ABSTRACT Various embodiments disclose a urine collection device. In one embodiment, a urine collection device includes a neck and a collection bag. The collection bag includes a main body disposed below the neck. The main body extends laterally away from the neck and is continuous with the neck. The urine collection device further includes a retention band that is disposed in an upper region of the neck. The retention band is formed from and circumscribes the upper region of the neck. The retention band includes a first fastening mechanism disposed on a first portion of the neck and a second fastening mechanism disposed on a second portion of the neck. The first fastening mechanism is configured to releasably mate with the second fastening mechanism when the first portion of the neck is overlapped with the second portion of the neck.

11 Claims, 8 Drawing Sheets

URINE COLLECTION DEVICE

BACKGROUND

The present disclosure generally relates to urine collection devices, and more particularly relates to an adjustable, resealable, and user configurable urine collection device.

Urinary incontinence (UI) has been in existence for centuries and is a common condition resulting from a number of different causes. With the average lifespan of people increasing, the number of people affected has also increased. This condition is seen as highly distressing due to the fact that UI accidents, when occurring in the presence of others, can lead to high levels of embarrassment by the afflicted. Due to the uncontrollable nature of this condition, constant precautions must be taken in order to prevent accidental mishaps at inopportune times. While such mishaps are viewed as highly embarrassing, many conventional protective measures can lead to embarrassment in and of themselves. For instance, absorbent incontinence pads are often bulky and can be clearly seen in outline form under one's clothes. Additionally, they are uncomfortable and hot to wear, especially in warm weather. In general, the amount of protection provided is proportional to the discomfort and visibility of the protecting device.

BRIEF SUMMARY

In one embodiment, a urine collection device is disclosed. The urine collection device comprises a neck and a collection bag. The collection bag includes a main body disposed below the neck. The main body extends laterally away from the neck and is continuous with the neck. The urine collection device further comprises a retention band that is disposed in an upper region of the neck. The retention band is formed from and circumscribes the upper region of the neck. The retention band comprises a first fastening mechanism disposed on a first portion of the neck and a second fastening mechanism disposed on a second portion of the neck. The first fastening mechanism is configured to releasably mate with the second fastening mechanism when the first portion of the neck is overlapped with the second portion of the neck.

In another embodiment, a urine collection system is disclosed. The urine collection system comprises a collection bag. The collection bag comprises a neck and a main body disposed below the neck. The main body extends laterally away from the neck and is continuous with the neck. The urine collection system further comprises a retention band that is disposed in an upper region of the neck. The retention band is formed from and circumscribing the upper region of the neck. The retention band comprises a first fastening mechanism disposed on a first portion of the neck and a second fastening mechanism disposed on a second portion of the neck. The first fastening mechanism is configured to releasably mate with the second fastening mechanism when the first portion of the neck is overlapped with the second portion of the neck. The urine collection system also comprises a handheld adapter that is configured to be removably coupled to the neck of the collector bag. The handheld adapter is further configured to be held against a user's body to guide a flow of urine into the collector bag.

In yet another embodiment, a urine collection device is disclosed. The urine collection device comprises a neck and a collection bag. The collection bag includes a main body disposed below the neck. The main body extends laterally away from the neck and is continuous with the neck. The urine collection device further comprises a retention band that is disposed in an upper region of the neck. The retention band is formed from and circumscribes the upper region of the neck. The retention band comprises a first fastening mechanism disposed on a first portion of the neck and a second fastening mechanism disposed on a second portion of the neck. The first fastening mechanism is configured to releasably mate with the second fastening mechanism at various positions when the first portion of the neck is overlapped with the second portion of the neck. The urine collection device also comprises a retaining member disposed within the main body and comprises at least one of gelling and deodorizing materials. A wicking mechanism is coupled to the retaining member. A first portion of the wicking mechanism is disposed within the neck and a second portion of the wicking mechanism is disposed within the main body. The wicking mechanism is configured to wick fluid down to the retaining member and the at least one of gelling and deodorizing materials.

BRIEF DESCRIPTION OF THE SEVERAL VIEWS OF THE DRAWINGS

The accompanying figures where like reference numerals refer to identical or functionally similar elements throughout the separate views, and which together with the detailed description below are incorporated in and form part of the specification, serve to further illustrate various embodiments and to explain various principles and advantages all in accordance with the present disclosure, in which.

DETAILED DESCRIPTION

One or more embodiments provide a cost effective device for capturing and collecting urine. Its purpose is to avoid soiling of clothing in the event of unplanned releases of urine, primarily for men with urinary incontinence. It also includes a mechanism for supporting use by women. One or more embodiments are advantageous over conventional devices because they accommodate a wide range of male anatomy dimensions. Another advantage is a design that naturally aligns with the male anatomy to minimize strains and pressure. This capability is designed for both erect and relaxed postures of the penile shaft. Another improvement is conformance to the shape of brief underwear for auxiliary support of a filled device. A further advance is a liner to reduce perspiration caused by direct contact of the skin with the material of the device. One or more embodiments utilize gelling and deodorizing materials to reduce mobility of any released fluids. For even better utility, it is adaptable for handheld use by either males or females. One or more embodiments have the further advantage of being manufactured with few components for lower cost. Embodiments also have the advantage of being easy to apply in a seated or standing position without having to remove clothing.

Various embodiments define a naturally-fitting urinary collection system having a waterproof bag with an integral retention band and jelling and deodorizing materials for reducing the effects of inadvertent urine leakage. In at least one embodiment, the urine collection system is built around a flexible and waterproof bag that has an integral retention band for attaching the system to a man's penile shaft. Making the band part of the bag reduces one or more steps in manufacturing and allows production of a less expensive product. The retention band has releasable mating materials that allow users to attach the band at a level of compression that facilitates both retention and comfort. The shape of the bag is defined such that the neck aligns to the angle of exit of a relaxed penile shaft from the pelvis. The acute angle of the neck is in relation to the central axis of the body of the bag. The top of the bag is further curved to fit around and under the man's genitals and between his legs. Another advance in this design is that the lower portion of the main body of the bag is curved to match the approximate curvature of briefs style underwear. Such underwear is an auxiliary method for supporting a bag that has collected copious amounts of urine. The collection bag is designed to fill with urine without stretching, a characteristic of a type of material that makes it less prone to ruptures or leaks.

Various embodiments of the device are manufactured in sizes handling capacities from 2 fluid ounces up to the full contents of an adult bladder. This smaller volume is commensurate with drips and minor incontinence problems. Urine released into the bag of the collection system reaches jelling and deodorizing materials contained within the lower section of the bag. These materials bind with the liquid and turn it into a gel. This reduces the prospects of a leak either from bag failures or through the attachment opening. Additional materials simultaneously deodorize the urine. When they are still dry, these jelling and deodorizing materials may be distributed in the bottom of the bag. An alternate embodiment contains the materials in a water soluble or permeable retaining member such as container, packet, capsule, and/or the like. Such containers allow urine to reach the materials, expanding the jelling materials as they absorb the urine. In one embodiment, a wick is attached to the container of the jelling and deodorizing materials. Such an attachment more effectively conveys urine from the area of the bag where urine is released.

Some embodiments include a liner attached to the inside of the bag near the opening to reduce contact between the material of the bag and the penile skin, which can become sensitive to some elastomeric materials. Another benefit of this liner is to wick moisture away from the skin to reduce discomfort of the user in prolonged use, in warm climates, or when clothing creates enough heat to cause perspiration. Other embodiments are manufactured without an inner liner to allow users to apply a separate sleeve to the penis prior to attaching the bag. This is advantageous for users who prefer a more cushioned sleeve, sleeves that contain topical medications or ointments, or sleeves with enhanced adhesive properties.

Another advantage of one or more embodiments is the ability to release captured air from the bag through a small opening. In this embodiment, the configuration of the retention band, when engaged by joining the releasable materials, forms a small opening next to the band to allow trapped air to be released from the bag. Release of this air when first attaching the urine collection system is useful to more easily fit the body of the bag between the legs and cause minimal rubbing in use. Furthermore, when urine is released into the present invention, the urine fills the inside cavity of the bag, interacting with the jelling and deodorizing materials. To use the bag most efficiently for its given volume, release of trapped air is conveniently done through the small opening at the top near the band.

In yet another embodiment, the urine collection system attaches to an adapter instead of to a person. In this embodiment, the retention band attaches to a tubular portion of the adapter that is similar to a man's penile anatomy. This adapter is made of rigid materials and is designed with a wide opening to accommodate release of urine by females when held against the outside of a female's genital area. With the adapter employed, it is used in similar fashion by males without attaching to the body. Furthermore, the adapter is suitable for use by children who might otherwise not be dimensionally matched to use the urine collection system discussed in other embodiments. The tubular portion of the adapter has a ledge above which the retention band is affixed. This ledge provides additional retaining force for keeping the bag from detaching. In addition to the tubular portion for attaching the urine collection system, the adapter has elements on the back for engaging the thumb and 1 or more fingers. This allows a user to hold the adapter in place for use while still having one hand free. The benefit of this adapter is that is allows both females and males to release and collect urine at times when restroom facilities may not be available or convenient. It is optionally used by males who do not wish to attach the urine collection system directly to their anatomy. In this mode of operation, the adapter is held up to the body but is not attached directly as in other modes.

In still another embodiment, an external cover fits over the body of the bag of the present invention. The external cover provides insulation to reduce heat conduction from any urine released into the bag. Heat in this area can sometimes be perceived as a moist sensation implying a leak of urine. The external cover is preferably made of a liquid impermeable material to act as an additional barrier against the inadvertent escape of urine from the bag. Yet another benefit of this embodiment is that this cover isolates the skin of the inside parts of the legs from the materials of the bag. This isolation further minimizes the potential for allergic reaction to bag materials.

Figure 1:
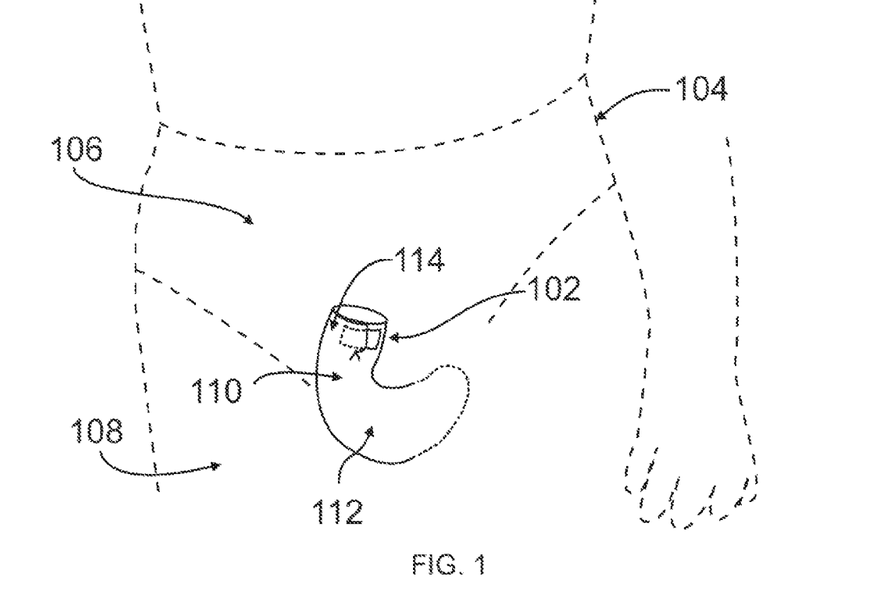
FIG. 1 is a perspective view of a urine collection device in an initially installed state according to one embodiment of the present disclosure.

Referring now to FIG. 1, an environmental view of a urine collection device 102 according to one embodiment of the disclosure is shown. FIG. 1 shows the device 102 as being worn by a user 104 within an inner garment 106 and an outer garment 108. The device 102 comprises a neck 110, a collection bag 112, and a retention band 114. The inner garment 106 can comprise, for example, underwear, an athletic supporter, compression shorts, and/or the like.

Figure 2:
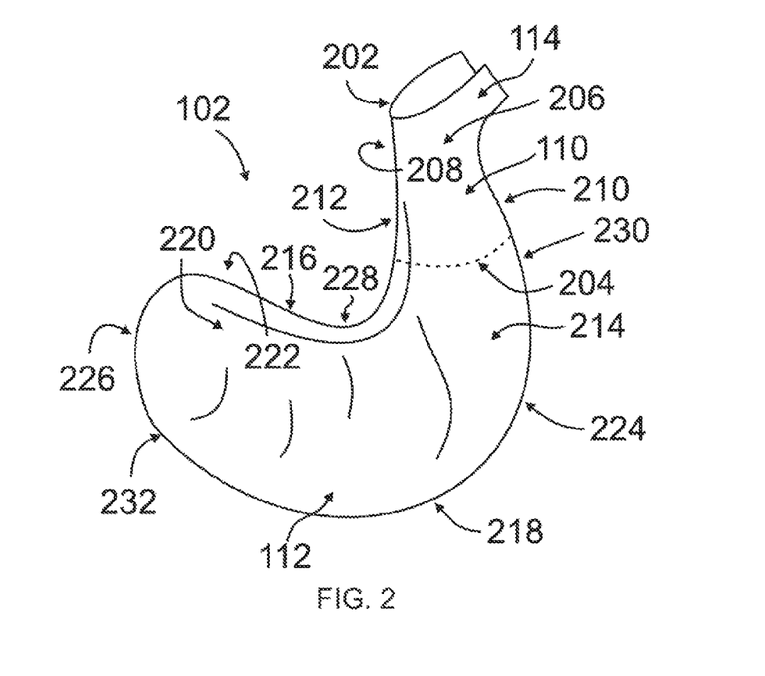
FIG. 2 is a side perspective view of a urine collection device according to one embodiment of the present disclosure.

FIG. 2 is a side perspective view of the urine collection device 102 showing one example of an overall shape and configuration of the device 102 according to one embodiment of the disclosure. In one embodiment, the neck/sleeve portion 110 of the device 102 is integrated into and continuous with the collection bag 112. Also, the retention band 114 is integrated into and continuous with the neck portion 110. At least the outer portion of the collection device 102 is made from a single piece of material (which can be multi-layered) or from multiple pieces of a material(s). In one embodiment, at least the neck 110, collection bag 112, and retention band 114 are made from a hypo-allergenic waterproof material that can be washable allowing it to be reused if desired.

In one embodiment, the neck 110 of the device 102 is generally cylindrical and comprises a top portion 202 (an area of the neck 110 that is closest to the user's pubic area when wearing the device 102), a bottom portion 204 situated opposite from the top portion 202, a first side portion 206, a second side portion 208 situated opposite from the first side portion 206, a front portion 210, and a rear portion 212 situated opposite from the front portion 210. The first and second side portions 206, 208 of the neck 110 transition into the front and rear portions 210, 212 of the neck 110. The various portions of the neck 110 define an empty space area within the neck 110.

In one embodiment, the collection bag 112 is comprised of a main body 214. The main body 214 comprises a top portion 216, a bottom portion 218 situated opposite from the top portion 216, a first side portion 220, a second side portion 222 situated opposite from the first side portion 220, a front portion 224, and a rear portion 226 situated opposite from the front portion 224. These portions of the main body 214 define an empty space area within the main body 214 that transitions into the empty space defined within the neck 110. In one embodiment, the first side portion 206 of the neck 110 transitions into the first side portion 220 of the main body 214; the second side portion 208 of the neck 110 transitions into the second side portion 222 of the main body 214; the front portion 210 of the neck 110 transitions into the front portion 224 of the main body 214; and the rear portion 212 of the neck 110 transitions into the top portion 216 of the main body 214.

In the configuration shown in FIG. 2 the neck 110 is substantially vertical or diagonal and extends upwards and curves back over the top portion 216 of the main body 214. In one embodiment, the neck rear portion 212 is substantially vertical or diagonal and transitions into the main body top portion 216. In this embodiment, the neck rear portion 212 comprises a configuration that curves inward from the neck top portion 202 towards the neck front portion 210 and then outward and away from the neck front portion 210 as the neck rear portion 212 transitions into the main body top portion 216. At the point of transition 228, the main body top portion 216 slopes upward to the top of main body rear portion 226.

Figure 3:
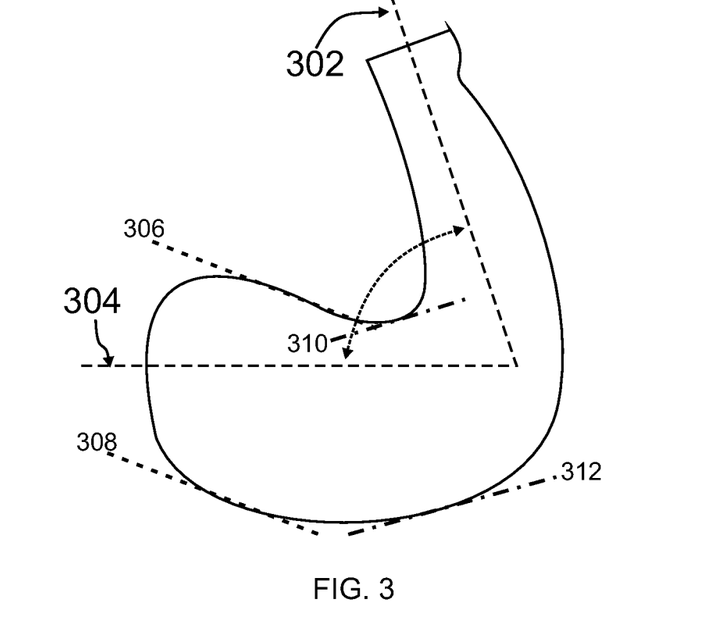
FIG. 3 is a side perspective view of the urine collection device of FIG. 2 showing an angular configuration of the device according to one embodiment of the present disclosure.

The neck front portion 210 is also substantially vertical or diagonal and transitions into the main body front portion 224. In one embodiment, the neck front portion 210 comprises a configuration that curves outward from the neck top portion 202 away from the neck rear portion 212 and then inward towards the neck rear portion 212 as it transitions into the main body front portion 224. At this point of transition 230, the main body front portion 224 curves outward and away from main body rear portion 226 and then towards the main body rear portion 226 as it transitions into the main body bottom portion 218. The main body bottom portion 218 comprises a configuration that curves downward away from the main body top portion 216 at the point of transition between the main body bottom portion 218 and the main body front portion 224. As the main body bottom portion 218 approaches the main body rear portion 226, the main body bottom portion 218 begins to curve upward and towards the main body top portion 216. At the point 232 of transition between the main body bottom portion 218 and the main body rear portion 226, the main body rear portion 226 comprises a configuration that curves outward and upward away from the front portion of the neck 110 and front portion 224 of the main body 214. As the main body rear portion 226 approaches the main body top portion 216, the main body rear portion 226 begins to curve upwards and inwards towards the main body top portion 216 and neck rear portion 212. In one embodiment, various regions of the top portion 216 and bottom portion 214 of the main body 214 are substantially parallel to each other as shown by the parallel dashed lines 306 and 308 and the parallel dashed-dotted lines 310 and 312 in FIG. 3.

The above configuration of the collection device 102 enables the neck 110 to extend diagonally upwards and back over the top portion 216 of the main body 214. The main body 214 extends laterally away from the neck rear portion 212. In one embodiment, the main body 214 is substantially horizontal to the ground when the collection device 102 is being worn by a standing individual. In another embodiment, the angle of the neck 110 is such that the at least a portion of the neck 110 extends over the main body 214. For example, the neck 110 is constructed at an acute angle represented by the dashed lines 302, 304 shown in FIG. 3, which is relative to the central angle of the main body 214. In one embodiment, this angle is between 65 to 80 degrees (e.g., 72 degrees) from the central bodyline and matches a range of angles representing the approximate angle at which the penile shaft emerges from the pubic area of a standing average adult male.

The main body bottom portion 218, in one embodiment, is rounded to follow the curvature of various undergarments that can be worn with the collection device 102. The area of transition 228 between the neck rear portion 212 and the main body top portion 216 sweeps down before turning back up at the transition area 232 between the main body top portion 216 and the main body rear portion 226 allowing room for the male scrotum in this area. The transition area 232 provides additional urine storage volume in an area between a man's legs and behind his genital area. It should be noted that the neck 110 and/or main body 214 of the collection device 102 can be manufactured in varying sizes to accommodate anatomies of different sizes. FIG. 2 also shows that the retention band 114 is continuous with the neck 110 of the main body 214 (collection bag). This provides many advantages such as a reduced number of manufacturing steps, a seamless integration to prevent irritations, etc.

Figure 4:
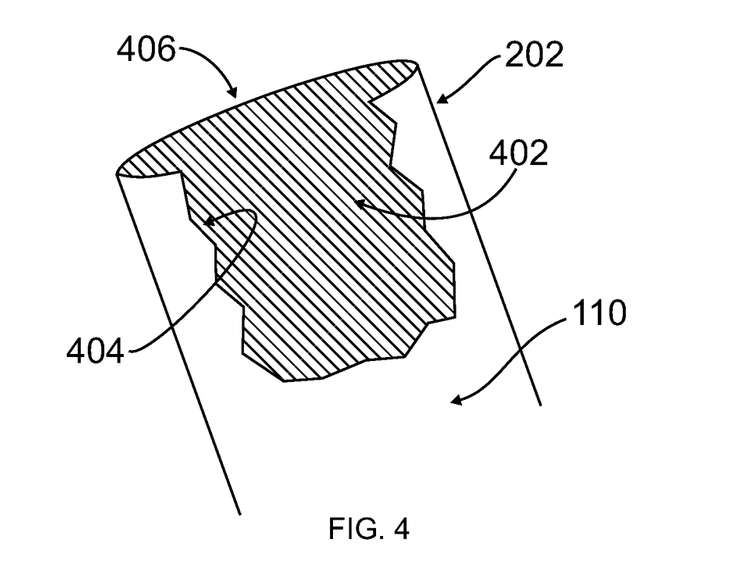
FIG. 4 is a cutaway view of a neck portion of the urine collection device of FIG. 2 showing an inner liner according to one embodiment of the present disclosure.
Figure 5:
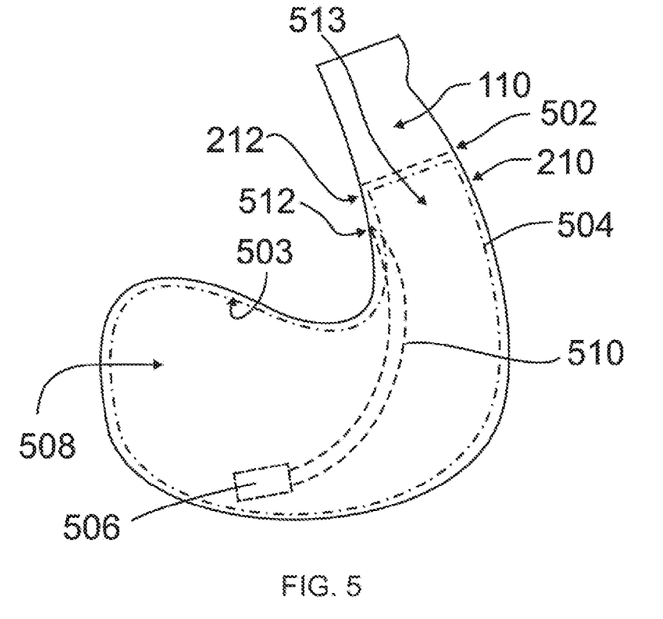
FIG. 5 is a side view of the urine collection device of FIG. 2 showing a container/capsule comprising gelling and deodorizing materials and a wicking mechanism according to one embodiment of the present disclosure.

In one embodiment, an inner liner 402 (FIG. 4) is fastened to an inner surface 404 of the neck 110 starting from an opening 406 in the neck top portion 202 to a position shown as dashed line 502 in FIG. 5. This position is low enough to reduce contact between the main body 214 and the penile skin. In one embodiment, the liner 402 is made of medically approved materials. The material of the liner 402 can be comprised of a breathable, hypoallergenic material that comprises wicking properties. The inner liner 402 draws moisture away from the surface of the skin into the liner 402 for quick evaporation. The liner 402 helps isolate potentially sensitive penile skin from the materials utilized in the collection device 102, minimizes the possibility of allergic reactions, and reduces sweating, which can all lead to skin irritation. The liner 402 also increases the holding power of the device 102 as well.

In one embodiment, an outer surface of the liner 402 comprises an adhesive that allows the liner 402 to be fixably or removably coupled/attached to the inner surface 402 of the neck 110. In another embodiment, the inner surface of the neck 110 and the outer surface of the liner 402 comprise a hook and loop fastening mechanism that allows the liner 402 to be removably coupled to the inner surface of the neck 110. Alternative methods such as stitching, tacking, and/or the like are also applicable as well. It should be noted that the liner material can also comprise an adhesive or an anti-slip material that contacts the penile shaft and improves retention when the main body 214 is filled with fluid. In one embodiment where a liner 402 is not utilized, the user is able to wrap a material around the penile shaft prior to putting on the urine collection device 102. This wrap material increases the holding power of the device 102 and also protects the user's skin. It should be noted that the wrap material can also be utilized in conjunction with the inner liner 402 as well.

In some embodiments, the collection device 102 comprises at least one of gelling and deodorizing materials, which can be separate or one in the same. These materials can be in a crystalline, powder, flake, or other form when dry. When a liquid such as urine comes into contact with the gelling material, this material absorbs the liquid and expands to reduce the amount of liquid within the collection device 102 and to keep the liquid away from the neck 110 of the device 102. The deodorizing material neutralizes and/or improves any odor emitting from the urine when the urine contacts the deodorizing material. In one embodiment, at least one of the gelling and deodorizing materials is embedded or impregnated into an optional inner liner 504 attached to at least the inner surface 503 of the main body 214. The inner liner 504 can be fixably or removably attached to the inner surface 503 of the main body 214 utilizing adhesive, hook and loop fasteners, and/or the like. In an embodiment where the main body inner liner 504 is removable, the inner liner 504 retains any fluids expelled into the device 102 allowing the collection device 102 to be reused with a new inner liner. In another embodiment, the main body inner liner 504 is not required and the gelling and deodorizing materials are embedded and/or impregnated into an inner and/or intermediate surface of the main body 214 itself.

In one embodiment, one or more of the gelling and deodorizing materials is maintained within a container/capsule 506 disposed within the empty space 508 defined by the main body 214 or optional main body liner 504. The container/capsule 506 can freely reside within the main body 214 or optional main body liner 504, or be fixably disposed therein. Various containers/capsules can be utilized to maintain the gelling and deodorizing materials. For example, a mesh-type container can be used to house the gelling and deodorizing materials where the container permits liquids to flow through while retaining crystals or other solids larger than openings in the mesh. This container ruptures by design with the expansion of the jelling materials. Another example of a container is a water-soluble container/capsule (e.g., comprised of water soluble/permeable paper or a gelatin-like material) that is designed to dissolve rapidly when exposed to liquids. This dissolving action releases the gelling and deodorizing materials to bond with the liquid such as urine.

In another embodiment, a wicking mechanism 510 is disposed within the empty space 508 defined by the main body 214 or optional main body liner 504 and is coupled to or situated above the container/capsule 506 comprising the gelling and deodorizing materials. In this embodiment, an upper portion 512 of the wicking mechanism 510 is attached to or at least angled towards the front or rear portions 210, 212 of the neck 110. In another embodiment, the upper portion 512 of the wicking mechanism 510 is not fixed and is angled towards an intermediate 513 area between the front or rear portions 210, 212 of the neck 110.

Figure 6:
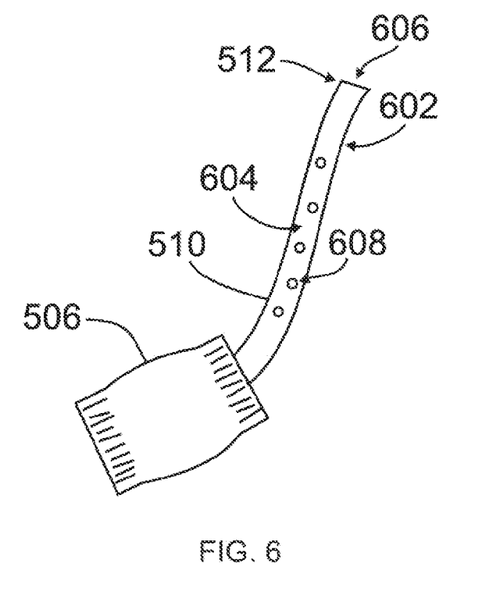
FIG. 6 shows a more detailed view of a container/capsule comprising gelling and deodorizing materials according to one embodiment of the present disclosure.

In one example, the wicking mechanism 510 comprises a solid or perforated outer surface 602 defining an inner hollow region 604, as shown in FIG. 6. As urine comes into contact with the wicking mechanism 510, the urine is drawn into the hollow region 604 through an opening 606 in the upper portion 512 of the mechanism 510 and/or through optional perforations/vias 608 situated throughout the outer surface 602. The urine flows into the hollow region 604 and is guided by the mechanism 510 where it contacts the container/capsule 506 comprising the gelling and deodorizing materials. In another embodiment, the wicking mechanism 510 comprises a wicking material that absorbs some of the urine being expelled into the collection device 102. The wicking mechanism 510 guides the absorbed urine down to the container/capsule 506 comprising the gelling and deodorizing materials. Upon contact with fluids, the container/capsule 506 opens or breaks down to allow the free release of the gelling and deodorizing materials. In another embodiment, the wicking mechanism 510 is impregnated with gelling and deodorizing materials that are freed from the wicking mechanism by contact with urine. In this embodiment, a separate container/capsule 506 is not needed.

Figure 7:
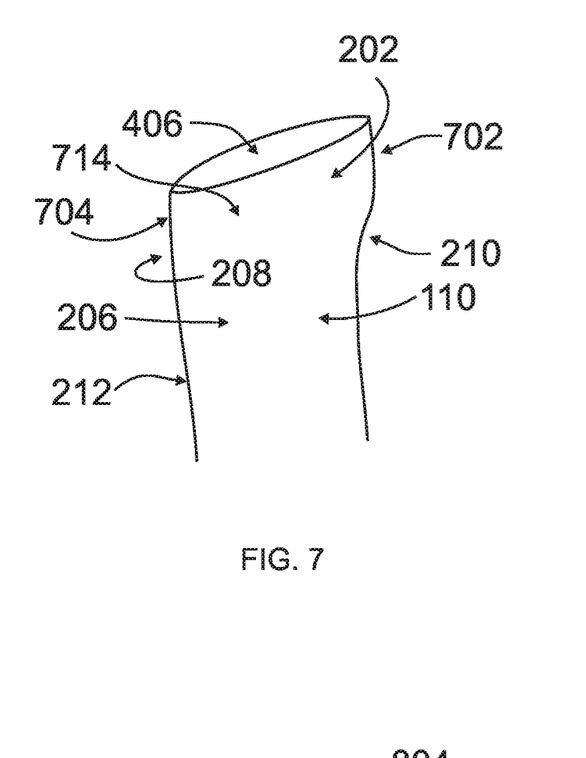
FIG. 7 is a side perspective view of a retention band according to one embodiment of the present disclosure.

FIG. 7 shows a side perspective view of a retention band 714 according to one embodiment. In this embodiment, the retention band 714 is continuous around the opening 406 in the top portion 202 of the neck 110. For example, the retention band 714 circumscribes and is formed from the side, front, and rear portions 206, 208, 210, 212 in the top area 202 of the neck 110. In one embodiment, a front portion 702 of the retention band 714 faces outward and away from the body of an average man wearing the collection device 102. This front portion 702 bulges/extends outward beyond the front portion 210 of the neck 110 providing the overlapping material that allows the wearer to adjust the fit/tightness of the band 714. It should be noted that the rear portion 704 of the band 714 can have a similar configuration as the front portion 702 and bulge/extend outward beyond the rear portion 212 of the neck 110.

Figure 8:
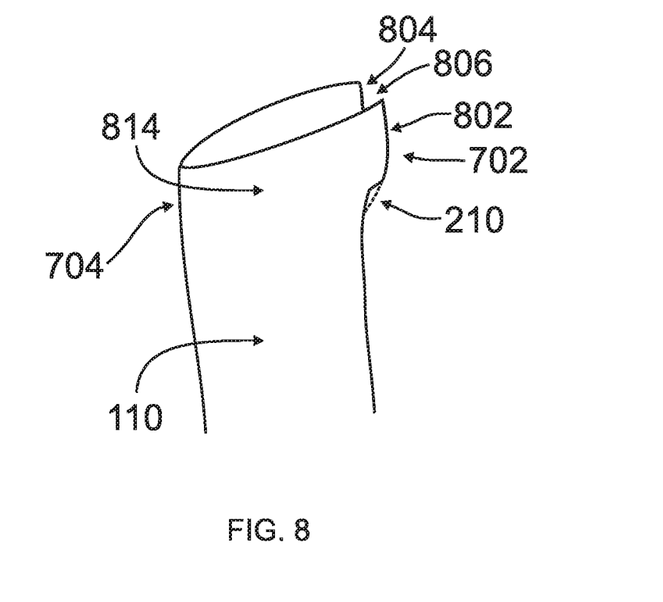
FIG. 8 is a side perspective view of a retention band according to another embodiment of the present disclosure.

In another embodiment, the integral retention band 814 is not continuous and comprises a separate right section 802 and a separate left section 804 disposed laterally opposite from the right hand section 802 in the front portion 702 of the band 814, as shown in FIG. 8. In this embodiment, the front portion 702 of the retention band 814 comprises a slit 806 that separates the right section 802 from the left section 804 of the band 814. This slit 806 can be formed in one of many stages of the manufacturing process and may be formed or manually produced as a post-forming step.

Similar to the embodiment discussed above, each area of the right section 802 and the left section 804 in the front portion 702 of the retention band 814 bulges/extends outward beyond and includes additional material around the front portion 210 of the neck 110 allowing the wearer to adjust the fit/tightness of the band 814 around his penile shaft. The retention band 814 can also comprise a slit (not shown) in the rear portion 704 of the retention band 114 creating a separate right section (not shown) and a separate left section (not shown) in the rear portion 704. If both the front and rear portions 702, 706 of the band 814 comprise a slit 806, a separate right section and a separate left hand section is formed between the front and rear portions 702, 704 of the band 814. In another embodiment, one of the front or rear portions 702, 704 comprises a separate left or right section, while the other of the front or rear portions 702, 704 is continuous and comprises a bulging/extended area as discussed above.

Figure 9:
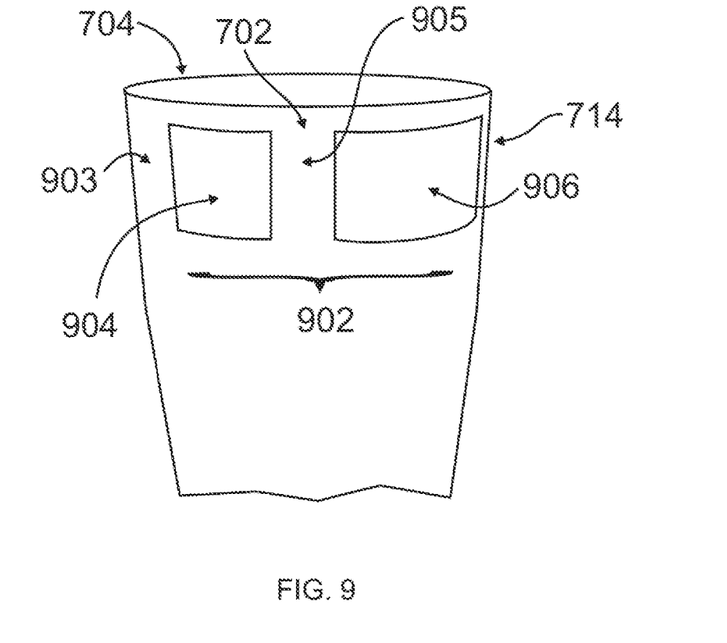
FIG. 9 is a front perspective view of the retention band in FIG. 7 in an open position according to one embodiment of the present disclosure.

FIG. 9 shows a front perspective view of the continuous retention band 714 in FIG. 7 with the band 714 in an open position. The open position allows the device to be more easily fitted onto a user's penile shaft. In one embodiment, a fastening mechanism(s) 902 is disposed on an outer surface 903 of the front portion 702, the rear portion 704, and/or the side portions of the retention band 714. In one embodiment, the fastening mechanism(s) 902 is formed as part of the neck and/or band material. In another embodiment, the fastening mechanism(s) 902 is attached to the neck and/or band material via adhesives, stitching, tacking, ultrasonic welding, and/or the like. Various fastening mechanism(s) 902 such as tethers/straps, elastic bands, hook and loop fasteners, adhesives, snaps, and/or the like can be utilized according to one or more embodiments. In the non-limiting example shown in FIG. 9, the fastening mechanism(s) 902 is a releasable securing mechanism comprising at least a first mating member 904 and a second mating member 906 disposed laterally opposite from the first mating member 904. In one embodiment the first mating member 904 is separated from the second mating member 906 by a gap 905. However, the first and second mating members 904, 906 can be different portions of a single mating member. The first mating member 904 comprises a material that is configured to releasably mate with the material of the second mating member 906. For example, the first and second mating members 904, 906 comprise hook and loop materials, adhesive materials, magnetic materials, and/or the like.

Figure 10:
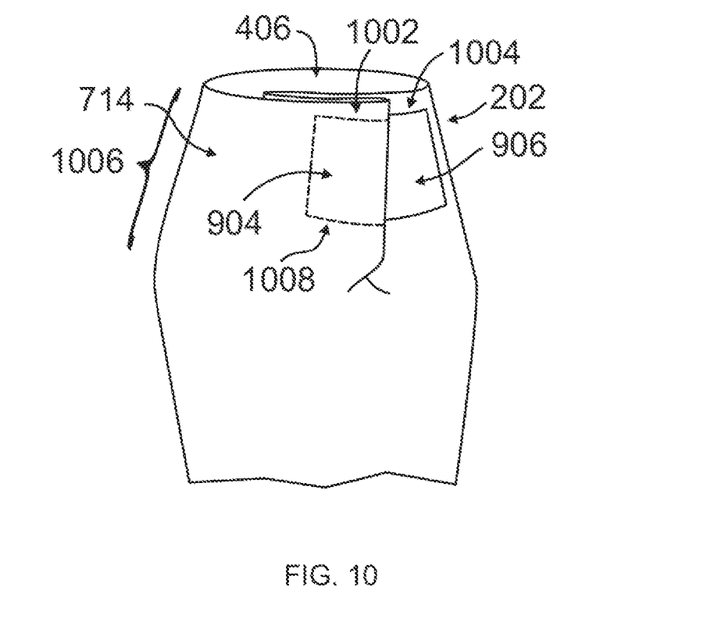
FIG. 10 is a front perspective view of the retention band in FIG. 7 in a closed position according to one embodiment of the present disclosure.

The user, in one embodiment, is able to adjust the fit or tightness of the continuous band 714 around his penile shaft by overlapping a first portion 1002 of the band 714 comprising the first mating member 904 with a second portion 1004 of the band 714 comprising the second mating member 906, as shown in FIG. 10. The overlapping configuration reduces the diameter of the opening 406 in the neck top portion 202, thereby securing the device 102 to the user. The dashed line 1008 shows the unseen outline of the first mating member 904 as it is being folded over. Region 1006 shows the top edge of retention band 714 that has been folded over.

Figure 11:
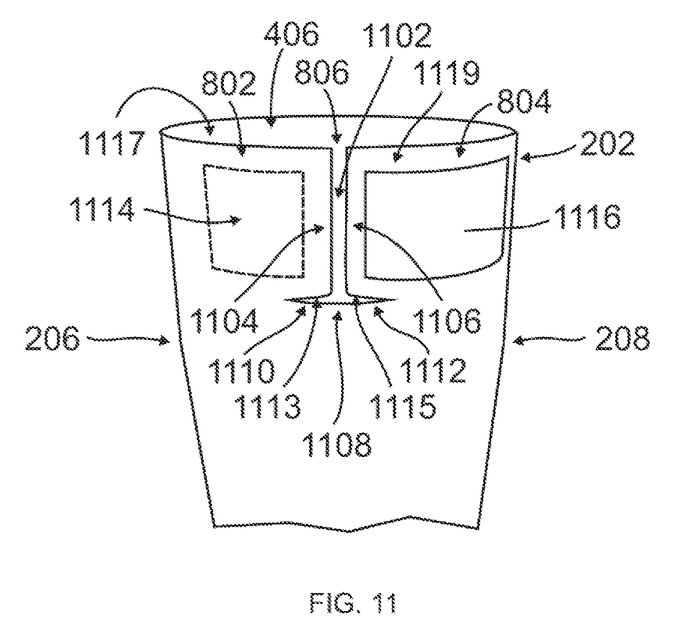
FIG. 11 is a front perspective view of the retention band in FIG. 8 in an open position according to one embodiment of the present disclosure.

FIG. 11 shows a front perspective view of the non-continuous retention band 814 shown in FIG. 8 with the band 814 in an open position. As discussed above, the non-continuous retention band 814 comprises a separate right section 802 and a separate left section 804 disposed laterally opposite from the right hand section 802 in the front portion 702 of the band 814. A slit or slitted area 806 separates the right section 802 from the left section 804 of the band 814. The wide opening of the retention band facilitated by the slit improves ease of application and removal. In one embodiment, the slit 806 comprises a first portion 1102 defining and separating a sidewall 1104, 1106 of the right and left sections 802, 804 respectively of the band 814. A second portion 1108 of the slit produced along a lower edge of the front portion 210 of the neck 110 where the neck is reducing in diameter. The second portion 1108 of the slit defines a lower edge 1110, 1112 of the right and left sections 902, 904 of the band 914. The lower edges 1110, 1112 extend from a bottom portion 1113, 1115 of the sidewalls 1104, 1106 toward the side portions 206, 208 of the neck 110. In one embodiment, the first portion 1102 of the slit 806 transitions into the second portion 1108 of the slit 806. The first portion 1102 of the slit 806 extends from the opening 406 in the neck top portion 202 to the second portion 1108 of the slit 806 to form the open front of the retention band 814.

The open position shown in FIG. 11 allows the device 102 to be more easily fitted onto a user's penile shaft. In one embodiment, a first fastening member 1114 is disposed on right section 802 of the band 814, and a second fastening member 1116 is disposed on the left section 804 of the band 814. In one embodiment, one of the first and second fastening members 1114, 1116 is disposed on an inner surface 1117 of the right or left section 802, 804 of the band 814, respectively. In this embodiment, the other of the first and second fastening members 1114, 1116 is disposed on an outer surface 1119 of the other of the right or left section 802, 804 of the band 814, respectively.

In one embodiment, the fastening members 1114, 1116 are formed as part of the neck and/or band material. In another embodiment, the fastening members 1114, 1116 are attached to the neck and/or band material via adhesives, stitching, tacking, ultrasonic welding, and/or the like. Various fastening mechanisms such as tethers/straps, elastic bands, hook and loop fasteners, adhesives, snaps, and/or the like can be utilized according to one or more embodiments. In the non-limiting example shown in FIG. 11, the fastening members 1114, 1116 are releasable securing mechanisms disposed laterally opposite from each other. The first fastening mechanism 1114 comprises a material that is configured to releasably mate with the material of the second fastening mechanism 1116. For example, the first and second fastening members 1114, 1116 comprise hook and loop materials, adhesive materials, magnetic materials, and/or the like.

Figure 12:
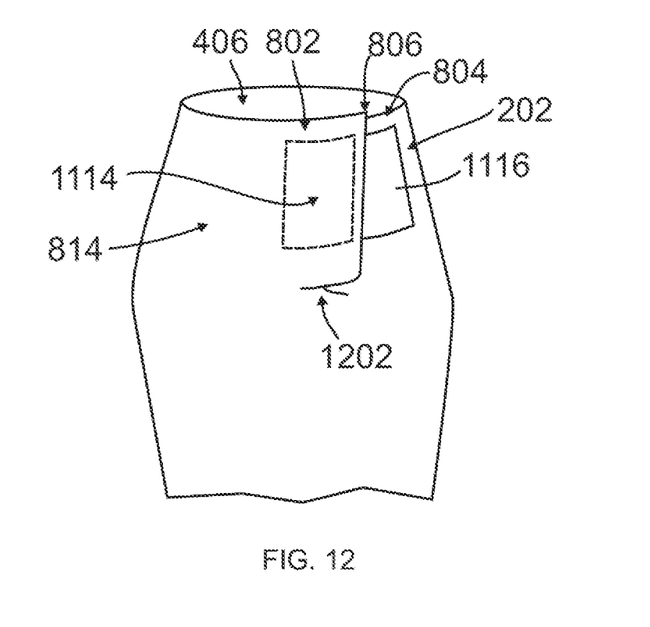
FIG. 12 is a front perspective view of the retention band in FIG. 8 in a closed position according to one embodiment of the present disclosure.

The user, in one embodiment, is able to adjust the fit or tightness of the band 814 around his penile shaft by overlapping the right (or left) section 802 of the band 814 with the left (or right) section 804 of the band and mating the first fastening member 1114 with the second fastening member 1116, as shown in FIG. 12. The overlapping configuration reduces the diameter of the opening 406 in the neck top portion 202, thereby securing the device 102 to the user. Mating the two releasable securing materials on fastening members 1114, 1116 forms a small opening 1202 at the base of the slit 806 next to the band 814. This opening 1202 allows trapped air to be released from the bag after initial application or after release of urine.

In one or more embodiments, the retention band 114 is not integrated into the neck 110 and is separate from the neck 110 and the collection bag 112. Also, in embodiments where the retention band 114 is an integrated band an external separate retention hand can be utilized in conjunction with the retention band 114 to provide additional support. In these embodiments, the retention band comprises a fastening mechanism(s) similar to that discussed above. A user places the retention band around the neck 110 of the device 102 and couples each portion of the fastening mechanism(s) together at the desired position. In another embodiment, a retention band such as that discussed in U.S. Pat. No. 8,187,238, which is hereby incorporated by reference in its entirety, is utilized with the urine collection device 102.

Figure 13:
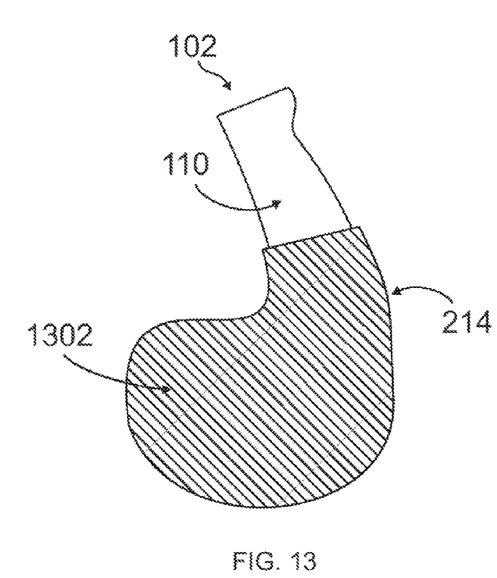
FIG. 13 is a side view of urine collection device comprising an optional outer protective cover according to one embodiment of the present disclosure.

FIG. 13 shows one example of an external cover 1302 that fits over the main body 214 of the collection device 102 according to one embodiment. The external cover 1302 provides insulation from portions of the user's body. Another purpose of the cover 1302 is to act as an additional barrier against the inadvertent escape of urine from the main body 214. This external cover 1302 can take the form of a lightweight fabric or of a thicker woven material. Alternatively, the external cover 1302 can be sprayed on an outer surface of the main body 214. The purpose in each case is to insulate the inner portion of a user's legs from contact with the main body material. This reduces the feeling of warmth from expelled urine and isolates the skin from the bag material to avoid any chance of an allergic reaction. Another feature of this cover 1302 is that it acts as an additional barrier against the inadvertent escape of urine from the main body 214 through a rupture, puncture, or some other cause. One embodiment of the external cover 1302 with a waterproof external layer retains released fluids between the main body 214 and the outermost external layer.

One or more embodiments also provide an adapter for use with the collection device 102 discussed above. The adapter allows female or handheld use of the collection device 102. The handheld adapter provides females and males the opportunity to hygienically release and collect urine at times when restroom facilities may not be available or convenient. In this embodiment, the adapter in use is held up to and not affixed to the human body.

Figure 14:
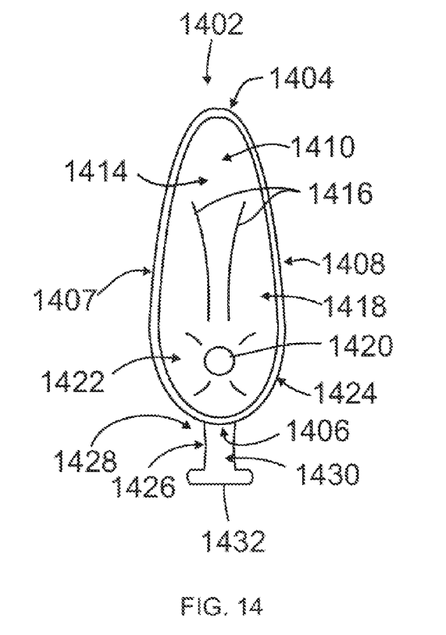
FIG. 14 is a front view of an adapter for a urine collection device according to one embodiment of the present disclosure.

FIG. 14 shows a front view of one example of an adapter 1402 for use with the collection device 102 discussed above. The adapter 1402 comprises a top portion 1404, a bottom portion 1406 situated opposite the top portion 1404, a first side portion 1407, and a second side portion 1408 situated opposite the first side portion 1407. The first and second side portions 1407, 1408 transition into the top and bottom portions 1404, 1406 of the adapter 1402. In this non-limiting example, the top portion 1404 of the adapter 1402 comprises a width that is less/narrower than a width of a bottom portion 1406 of the adapter 1402 situated below the top portion 1404 when the adapter 1402 is attached to the collection device 102.

The adapter 1402 also comprises a front portion 1410 and a rear portion 1512 (FIG. 15) situated opposite the front portion 1410. The first and second side portions 1407, 1408 also transition into the front and rear portions 1410, 1512 of the adapter 1402 as well. The front portion 1410 of the adapter 1402 comprises an opening 1414 configured with a shape that conforms generally to the female genital area while comprising a width sufficient to capture emissions of urine. The shape of the opening 1414 is also configured to allow discrete enclosure of the male genital area as well. Channels 1416 are formed on an inner surface 1418 of the adapter 1402 defined by the top, bottom, sides, front, and rear portions 1404, 1406, 1407, 1408, 1410, 1412, 1512 of the adapter. The channels 1416 guide urine to a drain opening 1420 in a lower portion 1422 of the adapter 1402. An optional cushion (cushioned member) 1424 expands the conforming range of the opening 1414 and makes use more comfortable. In one embodiment, the cushion 1424 circumscribes areas of the top, bottom, and side portions 1404, 1406, 1407, 1408 in the front portion/area 1410 of the adapter 1402 closest to the user's skin when the adapter 1402 is in use. In this embodiment, the cushion 1424 makes contact with the user's skin.

The adapter 1402 also comprises an adapter port 1426 disposed in a bottom rear region 1428 of the adapter 1402. The adapter port 1426 extends downward away from the bottom portion 1406 of the adapter 1402. In one embodiment, the adapter port 1426 comprises a cylindrical body 1430 and an annular end member 1432 comprising a diameter that is larger than the diameter of the body 1430. In one embodiment, the adapter port 1426 functions in the role of a male penile shaft for allowing the mechanical attachment of the collection device 102 to the adapter 1402. The retention band 114 is tightened around the body/neck 1430 of the adapter port 1426 and is held in place against the annular end member (ledge) 1432.

Figure 15:
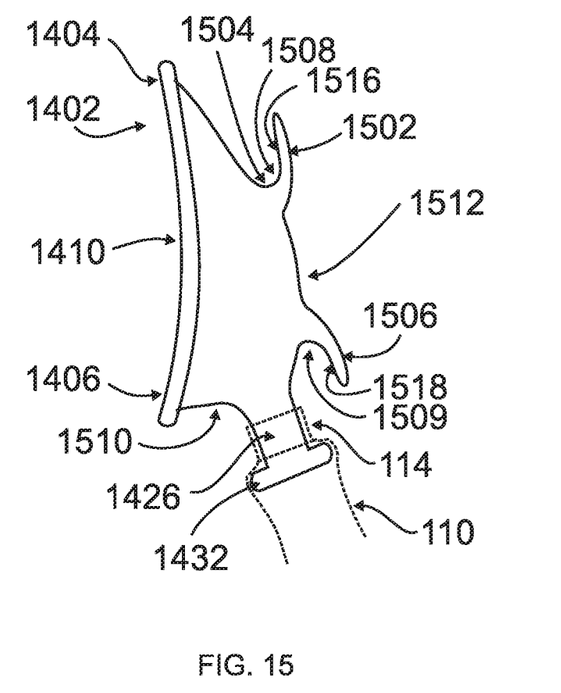
FIG. 15 is a side view of the adapter in FIG. 14 according to one embodiment of the present disclosure.

The rear portion 1512 of the adapter 1402 comprises a first extending/protruding member 1502. The first extending member 1502 comprises a curved configuration allowing the user to rest his/her thumb or finger(s) against the first extending member 1502. In one embodiment, the rear portion 1512 of the adapter 1402 slopes downward from the top 1404 of the adapter 1402 to a bottom portion 1504 of the first extending member 1502. In one embodiment, the rear portion 1512 of the adapter 1402 also comprises a second extending/protruding member 1506 disposed below the first extending member 1502. The second member 1506 comprises a curved configuration allowing the user to rest his/her fingers against the second extending member 1506.

The first and second extending members 1502, 1506 comprise opposite configurations such that the first extending member 1502 extends towards the top portion 1404 of the adapter 1402 while the second extending member 1506 extends towards the bottom portion 1406 of the adapter 1402. Each of the first and second extending members 1502, 1506 comprise a finger resting area(s) 1508, 1509 for the user's finger(s) or thumb to grip the extending member 1502, 1506. The finger resting area(s) 1508, 1509 is formed from the rear portion 1512 of the adapter 1402 and an inner area 1516, 1518 of the member 1502, 1506. The second extending member 1506 allows the user to rest, for example, his/her fourth or fifth finger in finger resting area 1509. A user may alternatively rest a thumb or index finger in finger resting area 1508, a middle or fourth finger in finger resting area 1509, and a small finger in area 1510.

In another embodiment, the rear portion 1512 of the adapter 1402 comprises a handle (not shown) instead of or in addition to the second extending member 1506. The handle is disposed at least partially below the first extending member 1502. The handle is configured to allow the user to place one or more fingers in a void defined by the handle while gripping the handle itself. This provides the user with a secure grip on the adapter 1402. In an alternate embodiment (not shown), the extending member(s) 1502, 1506, the optional handle, and the finger enclosing space(s) are not required. In this embodiment, the adapter is cradled in the hand with one or more fingers around the adapter port 1426.

Non-Limiting Examples

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A urine collection device comprising:
   a neck;
   a collection bag comprising a main body disposed below the neck, the main body extending laterally away from the neck and comprising an end portion that curves upwards towards the neck, the collection bag further comprising at least a pre-configured partial C-shape that situates at least a portion of the main body under a user's genital area and between the user's legs, and where the main body is continuous with the neck; and
   a retention band disposed in an upper region of the neck, the retention band being formed from and circumscribing the upper region of the neck, the retention band comprising a first fastening mechanism disposed on a first portion of the neck and a second fastening mechanism disposed on a second portion of the neck, where the first and second portions of the neck have a continuous circumference around the neck, and where the first fastening mechanism is configured to releasably mate with the second fastening mechanism when the first portion of the neck is overlapped with the second portion of the neck.

2. The urine collection device of claim 1, wherein the neck comprises a top portion, a bottom portion situated opposite the top portion, a first side portion, a second side portion situated opposite the first side portion, a front portion, and a rear portion situated opposite the front portion.

3. The urine collection device of claim 2, wherein the main body comprises a top portion, a bottom portion situated opposite the top portion, a first side portion, a second side portion situated opposite the first side portion, a front portion, and a rear portion situated opposite the front portion, where the first and second side portions of the main body are continuous with and transition into the first and second side portions of the neck, respectively, where the front portion of the main body is continuous with and transitions into the front portion of the neck, and where the top portion of the main body is continuous with and transitions into the rear portion of the neck.

4. The urine collection device of claim 3, wherein the top and bottom portions of the main body are substantially parallel with each other.

5. The urine collection device of claim 1, wherein the neck comprises a curved configuration where at least a portion of the neck extends over the main body.

6. The urine collection device of claim 1, further comprising:
   at least one of gelling and deodorizing materials disposed within the main body.

7. The urine collection device of claim 6, further comprising:
   a retaining member comprising the at least one of gelling and deodorizing materials.

8. The urine collection device of claim 7, further comprising:
   a wicking mechanism disposed within the neck and the main body, the wicking mechanism being coupled to the retaining member and configured to wick fluid down to the retaining member and the at least one of gelling and deodorizing materials.

9. The urine collection device of claim 1, further comprising:
   a removable inner liner disposed on and circumscribing an inner surface of at least a portion of the neck.

10. The urine collection device of claim 1, where the retention band is continuous with the neck.

11. A urine collection device comprising:
    a neck;
    a collection bag comprising a main body disposed below the neck, the main body extending laterally away from the neck and comprising an end portion that curves upwards towards the neck, at least a portion of the neck comprising an acute angle relative to a central axis of the main body, the collection bag further comprising at least a pre-configured partial C-shape that situates at least a portion of the main body under a user's genital area and between the user's legs, and where the main body is continuous with the neck;
    a retention band disposed in an upper region of the neck, the retention band being formed from and circumscribing the upper region of the neck, the retention band comprising a first fastening mechanism disposed on a first portion of the neck and a second fastening mechanism disposed on a second portion of the neck, where the first and second portions of the neck have a continuous circumference around the neck, and where the first fastening mechanism is configured to releasably mate with the second fastening mechanism at various positions when the first portion of the neck is overlapped with the second portion of the neck;
    a retaining member disposed within the main body, the retaining member comprising at least one of gelling and deodorizing materials therein, wherein the retaining member is separate and distinct from the main body and the neck; and
    a wicking tube coupled to at least an outer surface of the retaining member, the wicking tube comprising a structure having an outer surface and an inner surface circumscribing a hollow region, the wicking tube further comprising a plurality of vias extending from the outer surface of the wicking tube to the hollow region where a first portion of the wicking tube is disposed within and coupled to the neck and a second portion of the wicking tube is disposed within the main body, the wicking tube being configured to wick fluid down through the hollow region and into the retaining member and the at least one of gelling and deodorizing materials.

* * * * *